Figure 2:
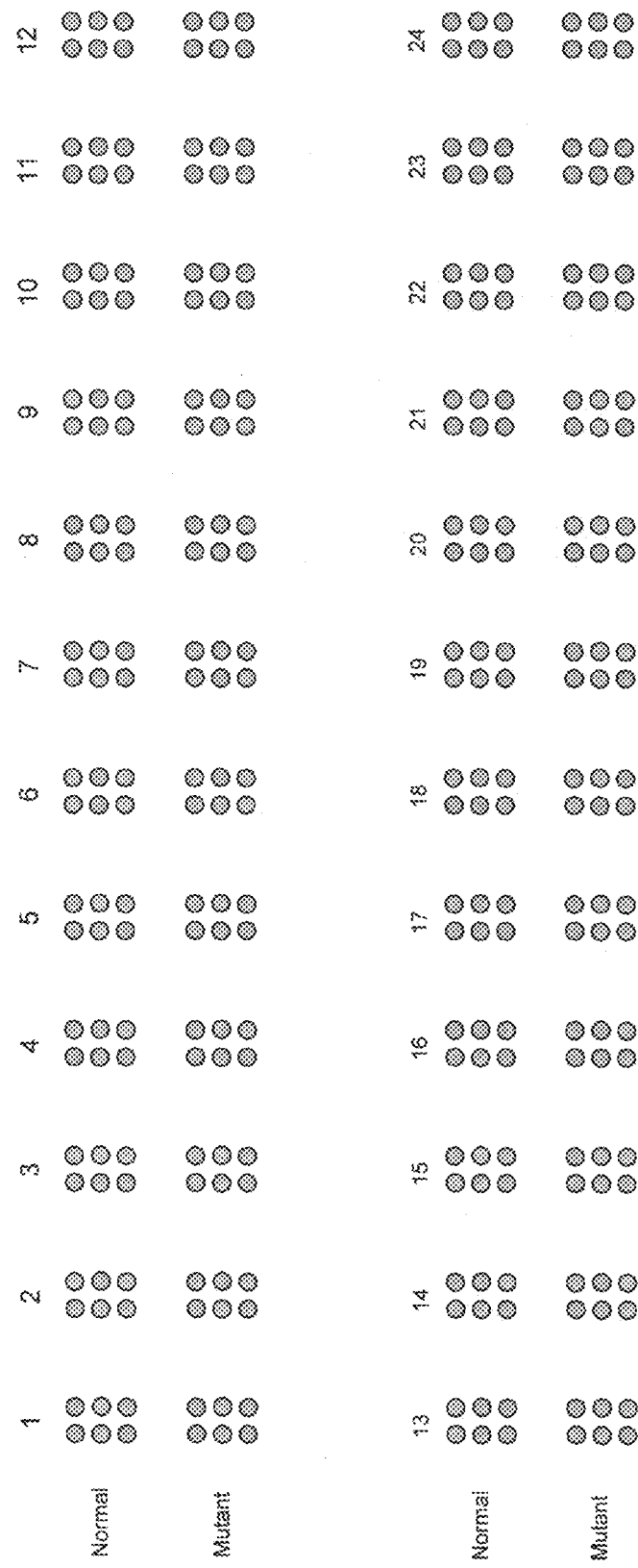
Figure 3:
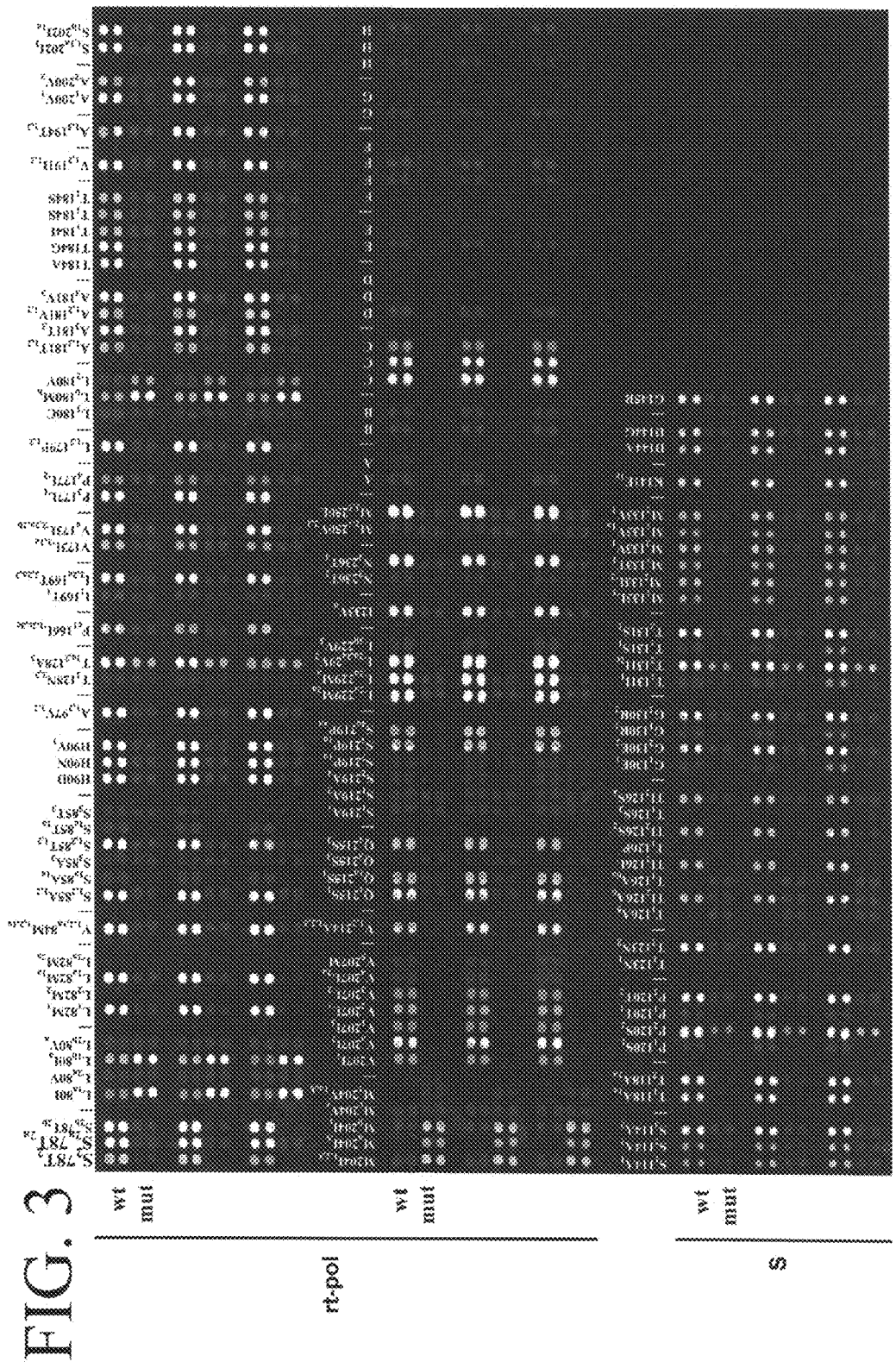

US009879330B2

(12) United States Patent
Chan et al.

(10) Patent No.: US 9,879,330 B2
(45) Date of Patent: Jan. 30, 2018

(54) HEPATITIS B VARIANTS WITH REDUCED SENSITIVITY TO THERAPEUTIC COMPOUNDS, THEIR DETECTION AND USES THEREOF

(75) Inventors: Kaimin Chan, Hong Kong (HK); Vivian Nap Yee Chan, Hong Kong (HK); Ching Lung Lai, Hong Kong (HK); Man Fung Yuen, Hong Kong (HK)

(73) Assignee: VERSITECH LIMITED, Hong Kong (HK)

( * ) Notice: Subject to any disclaimer, the term of this patent is extended or adjusted under 35 U.S.C. 154(b) by 1236 days.

(21) Appl. No.: 12/384,132

(22) Filed: Mar. 31, 2009

(65) Prior Publication Data

US 2009/0253123 A1 Oct. 8, 2009

Related U.S. Application Data

(60) Provisional application No. 61/042,721, filed on Apr. 5, 2008.

(51) Int. Cl.
*C12Q 1/70* (2006.01)
*C07K 14/005* (2006.01)
*A61K 38/00* (2006.01)

(52) U.S. Cl.
CPC .............. *C12Q 1/706* (2013.01); *A61K 38/00* (2013.01); *C07K 14/005* (2013.01)

(58) Field of Classification Search
CPC .. A61K 39/292; A61K 39/29; A61K 31/7088; C12Q 2565/627; C12Q 1/686; C12Q 1/706; C12Q 1/6837; C12Q 2561/113; C12Q 1/6827; C12Q 2523/319; C12Q 2600/156; C12Q 1/6883; C12Q 1/6818; C12Q 1/6825; C12Q 1/6844; C12Q 2531/113; C12Q 2563/103; C12Q 1/6876; C12Q 2535/125; C12Q 2535/131; C12N 2799/028; C12N 9/1276; G01N 33/532; G01N 2333/02; G01N 33/5764; G01N 21/6428; G01N 2800/44; G01N 33/56983; G01N 33/582; B01L 7/52
See application file for complete search history.

(56) References Cited

U.S. PATENT DOCUMENTS

| | | | | |
|---|---|---|---|---|
| 7,405,039 | B2 * | 7/2008 | Bartholomeusz et al. | 435/5 |
| 2003/0143527 | A1 * | 7/2003 | Shyamala | 435/5 |
| 2006/0165725 | A1 * | 7/2006 | Bozdayi | 424/227.1 |

OTHER PUBLICATIONS

Tang et al., Detection of hepatitis B virus genotypes using oligonucleotide chip among hepatitis B virus carriers in Eastern China, 2007, World Journal of Gastroenterology, vol. 13, No. 13, pp. 1975-1979.*
Song et al., Genotyping of hepatitis B virus (HBV) by oligonucleotides microarray, 2006, Molecular and Cellular Probes, vol. 20, pp. 121-127.*
Wang et al., Oligonucleotide chip, real-time PCR and sequencing for genotyping of hepatitis B virus, 2007, World Journal of Gastroenterology, vol. 12, No. 31, pp. 4260-4263.*
Wen et al., Oligonucleotide chip, real-time PCR and sequencing for genotyping of hepatitis B virus, 2004, Biosensors and Bioelectronics, vol. 19, pp. 685-692.*
Lewis et al., Sensitive in situ hybridisation technique using biotin-streptavidin-polyalkaline phosphatase complex, 1987, Journal of Clinical Pathology, vol. 40, pp. 163-166.*
Wen et al., A visual DNA chip for simultaneous detection of hepatitis B virus, hepatitis C virus and human immunodeficiency virus type-1, 2004, Biosensors and Bioelectronics, vol. 19, pp. 685-692.*
Naito et al., Rapid and Specific Genotyping System for Hepatitis B Virus Corresponding to Six Major Genotypes by PCR Using Type-Specific Primers, 2001, Journal of Clinical Microbiology, vol. 39, No. 1, pp. 362-364.*
Gan et al., DNA phosphorothioate modifications influence the global transcriptional response and protect DNA from double-stranded breaks, 2014, Scientific Reports, vol. 4, No. 6642, pp. 1-8.*
Wightman et al., Comparison of Sequence Analysis and a Novel Discriminatory Real-Time PCR Assay for Detection and Quantification of Lamivudine-Resistant Hepatitis B Virus Strains, 2004, Journal of Clinical Microbiology, vol. 42, No. 8, pp. 3809-3812.*
Allen, M. I., et al., "Identification and Characterization of Mutations in Hepatitis B Virus Resistant to Lamivudine" *Hepatology*, Jan. 9, 1998, pp. 1670-1677, vol. 27, No. 6.
Chan, K., et at., "A thalassaemia array for Southeast Asia" *British Journal of Haematology*, Oct. 24, 2003, pp. 232-239, vol. 124.
Galibert, F., et al., "Nucleotide sequence of the hepatitis B virus genome (subtype ayw) cloned in *E. coil" Nature*, Oct. 25, 1979, pp. 646-650, vol. 281.
Kazim, S. N., et al., "Association of core promoter mutations with viral breakthrough in chronic hepatitis B patients on long-term lamivudine therapy" *Journal of Gastroenterology and Hepatology*, Sep. 20, 2005, pp. 1525-1532, vol. 21.
Liaw, Y. F., et al., "Lamivudine for Patients with Chronic Hepatitis B and Advanced Liver Disease" *N. Engl. J. Med.*, Oct. 7, 2004, pp. 1521-1531, vol. 351, No. 15.
Perz, J. F., et al., "The contributions of hepatitis B virus and hepatitis C virus infections to cirrhosis and primary liver cancer worldwide" *Journal of Hepatology*, 2006, pp. 529-538, vol. 45.
Saiki, R. K., et al. "Primer-Directed Enzymatic Amplification of DNA with a Thermostable DNA Polymerase" *Science, New Series*, Jan. 29, 1988, pp. 487-491, vol. 239, No. 4839.

(Continued)

*Primary Examiner* — Benjamin P Blumel
(74) *Attorney, Agent, or Firm* — Saliwanchik, Lloyd & Eisenschenk

(57) ABSTRACT

The present invention is a diagnostic kit and materials for: 1) the prediction of the long-term response of a chronic hepatitis B virus (HBV) carrier to treatment with nucleoside/nucleotide analog, or their combination; 2) the detection of HBV variants that exhibit reduced reactivity to antibody detection; 3) the detection of HBV variants in the precore/core region that negatively affect the course of liver disease; 4) the identification of the HBV genotype.

13 Claims, 3 Drawing Sheets
(1 of 3 Drawing Sheet(s) Filed in Color)

(56) References Cited

OTHER PUBLICATIONS

Sato, S., et at, "Hepatitus B Virus Strains with Mutations in the Core Promoter in Patients with Fulminant Hepatitis" *Annals of internal Medicine*, Feb. 15, 1995, pp. 241-248, vol. 122, No. 4.

Stuyver, L. J., et at, "Nomenclature for Antiviral-Resistant Human Hepatitis B Virus Mutation in the Polymerase Region" *Hepatology*, Mar. 2001, pp. 751-757, vol. 33.

Torresi, J., et al, "Reducted Antigenicity of the Hepatitis B Virus HBsAg Protein Arising as a Consequence of Sequence Changes in the Overlapping Polymerase Gene That Are Selected by Lamivudine Therapy" *Virology*, Oct. 16, 2001, pp. 305-313, vol. 293.

Weber, B., "Genetic variability of the S gene of hepatitis B virus; clinical and diagnostic impact" *Journal of Clinical Virology*, 2005, pp. 102-112, vol. 32.

\* cited by examiner

FIG. 1

An example of spots arrangement of an array for naked eye detection with interrogation at 24 positions in 2 subarrays where a cluster of 3 x 2 dots forms a spot and the mutant oligonucleotide is printed immediately below the normal oligonucleotide.

HEPATITIS B VARIANTS WITH REDUCED SENSITIVITY TO THERAPEUTIC COMPOUNDS, THEIR DETECTION AND USES THEREOF

CROSS-REFERENCE TO A RELATED APPLICATION

This application claims the benefit of U.S. provisional application Ser. No. 61/042,721, filed Apr. 5, 2008, which is incorporated herein by reference in its entirety.

BACKGROUND OF THE INVENTION

Hepatitis B virus (HBV) infection is a serious global health problem affecting approximately 2 billion people worldwide. About 400 million people infected by HBV are chronic carriers. Each year, about 1 million people die of various HBV diseases such as chronic hepatitis, cirrhosis and hepatocellular carcinoma (HCC) (World Health Organization, 2000). The disease is relatively rare in Western countries, acquired mainly in adulthood. However, the disease is virtually endemic in Asian and African countries, where most chronic HBV infections are acquired perinatally or during childhood.

The hepatitis B virus (HBV) is a small DNA virus of about 3200 bases with extensive sequence variability. Currently eight genotypes (A to H) are recognized.

The virus can cause debilitating disease conditions. Acute infection may lead to liver failure, although it is rare. Hepatitis B infection develops into a chronic form in over 90% of those infected at birth or as infants. Chronic infection eventually lead to cirrhosis and carcinoma of the liver in 25-40% of the patients. HBV is estimated to cause 30% of cirrhosis and 50% of HCC globally (Perz et al., 2006). This enormous burden highlights the need for the development of effective antiviral therapy, which is useful in reducing the risk of HCC (Liaw et al, 2004). It is therefore important to monitor a patient's response to such therapy.

HBV is mainly spread vertically with the virus passed on from infected mothers to infants at birth. Infants can also be infected through close contact with infected parents and siblings. HBV is also spread horizontally by sexual contacts or close contact with infected blood.

The virus replicates via an RNA intermediate and utilizes reverse transcription that lacks proofreading capability in its replication strategy. The HBV genome is partially double stranded and encodes envelope, precore/core, reverse transcriptase/polymerase and X genes in four overlapping open reading frames.

The envelope protein antigen is referred to as HBsAg (hepatitis B surface antigen) and it makes up the outer surface coat of the virus. The core protein antigen is referred to as HBcAg (hepatitis B core antigen) and it forms the core of the virus that encapsulates the HBV DNA. The precore protein antigen is referred to as HBeAg (hepatitis B e antigen) with unknown function. The protein X antigen is referred to as HBxAg (hepatitis B x antigen) and its exact function is also unknown.

The polymerase gene overlaps the envelope gene. Thus, mutations affecting the catalytic domain of the polymerase gene can also affect the protein sequence of the envelope protein and vice versa.

Current treatments for chronic hepatitis B infection include interferon, and nucleoside/nucleotide analogues. Unfortunately, treatment with interferon has many side effects and only a small proportion of patients respond to therapy.

Nucleoside or nucleotide analogues are chemically engineered nucleotides developed to act as substitute building blocks to inhibit viral DNA synthesis during viral replication. Currently approved (in the US) nucleoside and nucleotide analogues for treatment of chronic hepatitis B are: lamivudine (3TC or LMV), telbivudine (L-dT), entecavir (ETV), adefovir (ADV) and tenofovir.

While these compounds have been effective at inhibiting HBV DNA synthesis, they require long-term treatment and there is the potential for resistant mutant HBV strains to emerge during prolonged treatment. In patients on long-term treatment with LMV, common resistance conferring mutations are rtM204I/V+/−rtL180M (Allen et al., 1998) as well as other mutations. In some patients, resistant viral strains carrying mutations in the B, C and D domains of the HBV DNA polymerase gene emerge upon prolonged therapy. These patients then have a higher risk of developing HCC, compared to LMV-treated patients without resistant virus.

Additionally, during the process of hepatitis B e-antigen (HBeAg) seroconversion, precore and core promoter mutants emerge due to selection under immune pressure. These precore mutants have been implicated as the cause of more severe HBV infections. Core promoter mutants, whilst causing a decrease in precore mRNA transcription and HBeAg production, enhance viral replication, are also related to the development of HCC.

Kazim et al. (2006) report that core promoter and YMDD motif mutations are associated with viral breakthrough in patients on long-term LMV therapy. Also, variants of the gene coding for the surface antigen has been found in HBV vaccinated children, in post liver transplantation patients receiving anti-HBV immunoglobulin therapy, in patients with occult infection (Weber, 2005) and in patients treated with LMV (Torresi et al., 2002).

The protection of HBV vaccination is based on the induction of antibodies against major antigenic epitopes of the HBV surface-antigen (HBsAg). For patients who have undergone liver transplantation for hepatitis B-related end-stage liver disease, prophylaxis against recurrent HBV infection is given by administration of hepatitis B immunoglobulins derived from vaccinated subjects. Again, the emergence of immune escape HBV mutants results in viral persistence in spite of adequate antibody titers.

The development of effective antiviral therapy therefore requires a method for monitoring the emergence of resistant strains of HBV and to develop assays to detect and identify these resistant viruses so that the clinician can make a timely switch to a different treatment regimen when resistance arises.

Many studies have addressed the prevalence of different genotypes throughout the world (Lindh, M, Anderson A S, Gusdal A. Genotypes, nt 1858 variants, and geographic origin of hepatitis B virus—large-scale analysis using a new genotyping method. J Infect Dis 1997; 175:1285-1293; Chan H L Y, Tsui S K W, Tse C-H, Ng E Y T, Au T C C, Yuen L, Bartholomeusz A, Leung K-S, Lee K-H, Locarnini S, Sung J J Y. Epidemiological and virological characteristics of 2 subgroups of hepatitis B virus genotype C. J Infect Dis 2005; 191:2022-2032; and Yuen M-F, Sablon E, Yuan H-J, Wong D K-H, Hui C-K, Wong B C-Y, Chan A O-O, Lai C L. Significance of hepatitis B genotype in acute exacerbation, HBeAg seroconversion, cirrhosis-related complications, and hepatocellular carcinoma. Hepatology 2003; 37:562-567) and the predisposition of different genotypes to disease complications such as development of cirrhosis, HCC (Kuang S Y, Jackson P E, Wang J-B, Lu P-X, Munoz A, Qian G-S, Kensler T W, Groopman J D. Specific mutations of hepatitis B virus in plasma predict liver cancer development. Proc Natl Acad Sci, USA 2004; 101:3575-3580; and Yuen M F, Sablon E, Wong D K H, Yuan H-J, Wong B C-Y, Chan A O O, Lai C L. Role of hepatitis B virus genotypes in chronic hepatitis B exacerbation. Clin Infect Dis 2003; 37:593-597) and response to treatment (Kao J H, Chen P J, Lai M Y, Chen D S. Hepatitis B genotypes correlate with clinical outcomes in patients with chronic hepatitis B. Gastroenterology 2000; 118:554-559; and Buti M, Cotrina M, Valdes A, Jardi R, Rodriguez-Frias F, Esteban R. Is hepatitis B virus subtype testing useful in predicting virological response and resistance to lamivudine? J Hepatol 2002; 36:445-446)

To aid in the management of hepatitis B patients, various test strips based on reverse dot blot (RDB) allele-specific oligonucleotide (ASO) hybridization technique were developed to identify either genotype (INNO-LiPA HBV genotyping. Innogenetics NV, Belgium) or mutations (INNO-LiPA HBV precore. Innogenetics NV, Belgium; and INNO-LiPA DR. Innogenetics NV, Belgium). Since RDB-ASO principle requires the same hybridization and washing conditions for all variants under analysis, all normal and mutant probes would need similar melting temperature (Tm) (Saiki R K, Walsh P S, Levenson C H, Erlich H A. Genetic analysis of amplified DNA with an immobilised sequence-specific oligonucleotide probe. Proc Natl Acad Sci, USA. 1989; 86:6230-6234). This poses limitations on testing >20 mutations/genotypes on a single RDB strip. Currently three separate test strips are needed to assess eight genotypes and 12 mutations (INNO-LiPA HBV genotyping. Innogenetics NV, Belgium; INNO-LiPA HBV precore. Innogenetics NV, Belgium; and INNO-LiPA DR. Innogenetics NV, Belgium). Other groups have devised oligonucleotide microarray/chip (H, Cho M, Hco J, Kim H, Jun H, Shin W, Cho B, Park H, Kim C. Oligonucleotide chip for detection of lamivudine-resistant Hepatitis B Virus. J Clin Microbiol 2004; 42:4181-4188; Mao H, Wang H, Zhang D, Mao H, Zhao J, Shi J, Cui Z. Study of hepatitis B virus gene mutations with enzymatic colorimetry-based DNA microarray. Clin Biochem 2006; 39:67-73; Song Y, Dai E, Wang J, Liu H, Zhai J, Chen C, Du Z, Guo Z, Yang R. Genotyping of hepatitis B virus (HBV) by oligonucleotides microarray. Mol Cell Probes. Epub 2006 January; and Li Z G, Chen L Y, Huang J, Qiao P, Qiu J M, Wang S Q. Quantification of the relative levels of wild-type and lamivudine-resistant mutant virus in serum of HBV-infected patients using microarray. J Viral Hepatitis 2005, 12:168-175), but the same RDB-ASO principle was employed. The maximum number of mutations detectable was 20.

SUMMARY OF THE INVENTION

The present invention provides materials and methods for: 1) the prediction of the long-term response of a chronic hepatitis B virus (HBV) carrier to treatment; 2) the detection of HBV variants in the precore/core region that exhibit reduced reactivity to antibody detection; 3) the detection of HBV variants that negatively affect the course of liver disease; and 4) the identification of the HBV genotype.

Advantageously, the subject invention provides a comprehensive HBV array for the simultaneous analysis of all, or most, of the HBV variants of interest. In one embodiment, this includes 8 HBV genotypes, 5 precore, 2 core-promoter mutations, and 23 S gene and 45 rt polymerase gene mutations. The use of this assay facilitates the rapid, easy, and accurate detection of viral mutants and genotypes in a patient's serum sample. In one embodiment, the results can be readily visualized by the naked eye, without the need for instrumentation.

In one embodiment, the present invention relates to the identification of hepatitis B viral variants that exhibit reduced sensitivity to nucleoside/nucleotide analogues. The subject invention also pertains to viral variants that exhibit reduced reactivity to immunological reagents such as antibodies to viral surface components. The invention further pertains to the identification of HBV variants that affect the course of liver disease. These variants include a genotype of the HBV and variants with mutations at the precore/core region, the S gene and the rt polymerase gene. The invention further provides assays that detect and monitor such variants and assays that are useful in monitoring antiviral therapeutic regimens.

Advantageously, in one embodiment, the present invention provides assays that monitor the emergence of HBV variants that are resistant or exhibit reduced sensitivity to LMV, other nucleoside/nucleotide analogue or their combination, and other anti-HBV agents or combination thereof. The identification of these HBV variants can be used to guide physicians to modify or to switch treatment protocols.

The present invention also makes it possible to identify HBV strains that exhibit reduced reactivity to antibodies. This includes HBV mutants that evade the host's immune response or escape immunoassay detection.

The present invention also provides assays to identify the genotypes of the HBV. The genotype of a patient's HBV can, for example, influence the course and severity of liver disease.

In one embodiment, the subject invention provides kits, materials, and processes for detecting HBV variants of interest, through the identification of specific viral markers.

BRIEF DESCRIPTIONS OF THE DRAWINGS

The file of this patent contains at least one drawing executed in color. Copies of this patent with color drawings(s) will be provided by the Patent and Trademark Office upon request and payment of the necessary fee.

Figure 1:
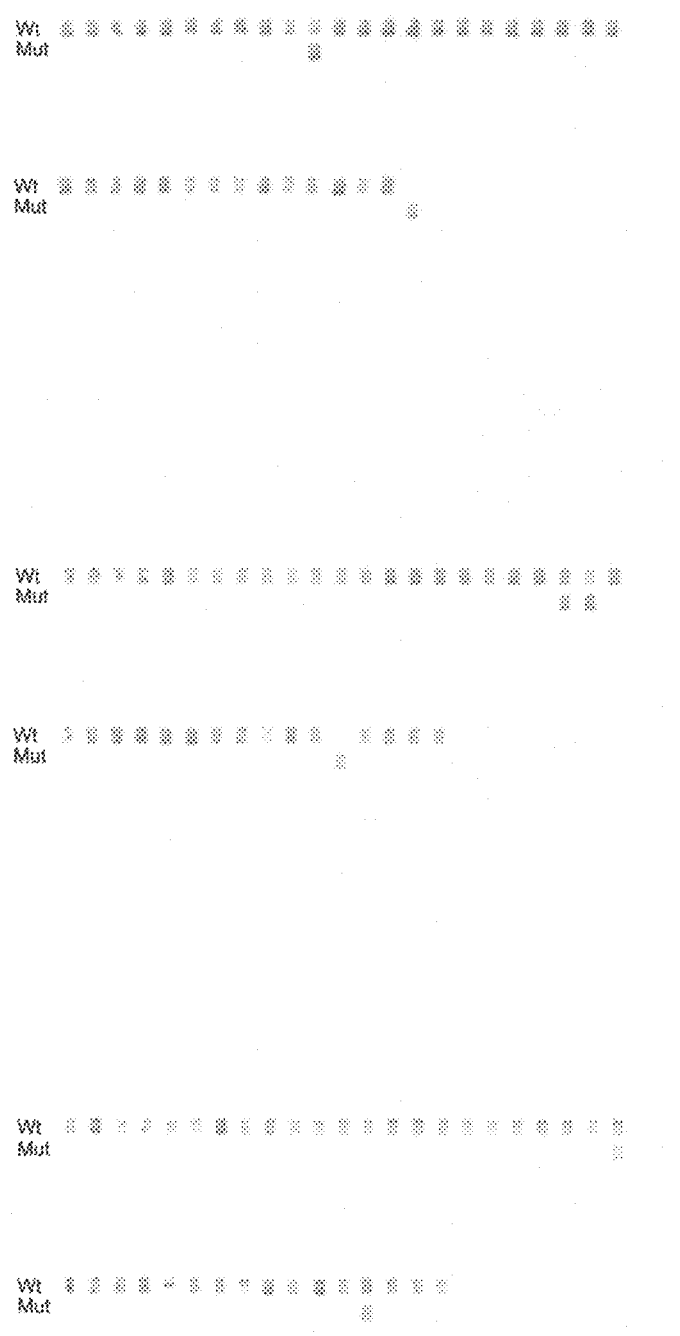

FIG. 1 is a photo of an array using the color detection method. For each set, the normal primers are on the top, and the mutant primers are underneath the normal primers, FIG. 2 is an example of spots arrangement of an array which is visible to the naked eye.

FIG. 3 is a HBV array showing the detection of various mutations.

DETAILED DESCRIPTION OF THE INVENTION

The present invention provides materials and methods for: 1) the prediction of the long-term response of a chronic hepatitis B virus (HBV) carrier to treatment; 2) the detection of HBV variants in the precore/core region that exhibit reduced reactivity to antibody detection; 3) the detection of HBV variants that negatively affect the course of liver disease; and 4) the identification of the HBV genotype.

In one embodiment, the present invention relates generally to hepatitis B viral variants that exhibit reduced sensitivity to nucleoside/nucleotide analogues both in vitro and in vivo. The subject invention also pertains to viral variants that exhibit reduced reactivity to immunological reagents such as antibodies to viral surface components. The invention further pertains to the identification of HBV variants that affect the course of liver disease. These variants include a genotype of the HBV and variants with mutations at the precore/core region. The invention further encompasses assays that detect and monitor such variants and assays that are useful in monitoring antiviral therapeutic regimens.

Advantageously, in one embodiment, the present invention provides assays that monitor the emergence of HBV variants that are resistant or exhibit reduced sensitivity to LMV, other nucleoside/nucleotide analogue or their combination, and other anti-HBV agents or combination thereof. The identification of these HBV variants can be used to guide physicians to modify or to switch treatment protocols.

The present invention also makes it possible to identify HBV strains that exhibit reduced reactivity to antibodies such as mutants that evade the host's immune response or escape immunoassay detection.

The present invention also provides assays to identify the genotype of the HBV. The genotype of a patient's HBV can influence the course and severity of liver disease.

Advantageously, the subject invention provides a comprehensive HBV array for the simultaneous analysis of all, or most, of the HBV variants of interest. In one embodiment, this includes 8 HBV genotypes, 5 precore, 2 core-promoter mutations, and 23 S gene and 45 rt polymerase gene mutations. The use of this assay facilitates the rapid, easy, and accurate detection of viral mutants and genotypes in a patients' serum sample. In one embodiment, the results can be readily visualized by the naked eye, without the need for instrumentation.

The subject invention can be practiced using any of a variety of methods for detecting viral markers. These methods include, for example, ARMS (amplification refractory mutation system) PCR, PCR or ARMS-PCR coupled with RFLP (restriction fragment length polymorphism), PCR plus hybridization such as reverse dot blot and allele specific primer extension among others.

Kits provided according to the subject invention would typically comprise one or more of the following: a glass slide (i.e., the HBV array) and cover slips for covering the sample, and reactants such as buffer, dNTPs and polymerase. The kits may also include the reagents used for naked eye detection, such as strepavidin-horse radish peroxidase/alkaline phosphatase, and a substrate for color development such as 5-bromo-4-chloro-3-indolyl phosphate (BCIP) and P-nitroblue tetrazolium chloride (NBT).

In one embodiment, the invention provides materials, kits and methods for detecting the viral markers for long-term response to treatment with LMV or other nucleoside/nucleotide analogues or their combination, for immune escape, and for genotyping. The methods can be practiced by, for example, extracting and amplifying HBV nucleic acids from a sample, and directly sequencing the amplified products to determine if such viral markers are present in the sample.

In another embodiment, the invention provides materials, kits and panels of oligonucleotides capable of detecting the viral markers, and for genotyping. In this embodiment the method can be practiced by, for example, reacting the amplified product from HBV nucleic acids to the panel of oligonucleotides complementary to the sequence of HBV genome that include the markers and then determining if the oligonucleotides hybridize to the nucleic acids or be extended.

The term mutation(s) is used in its broadest sense to include any nucleotide/amino acid substitution, addition, or deletion.

Mutations Associated with Failure to Respond to Treatment and/or Reduced Reactivity to Antibodies The subject invention provides methods for determining whether HBV extracted from a patient's biological sample, exhibits reduced sensitivity to LMV, ADV and to other nucleoside/nucleotide analogues, or other anti-HBV agents or combination thereof. In one embodiment this method involves isolating DNA or RNA from the HBV and screening for mutation(s) in the gene encoding HBV polymerase that result in at least one amino acid substitution, deletion or addition in the DNA polymerase. A further embodiment involves identifying mutations in the core or precore regions. In specific embodiments, these mutations are associated with altered viral replication, HBeAg expression and/or mutated HBeAg.

The amino acid positions for the HBV polymerase are numbered to be consistent with the nomenclature proposed by Stuyver et al. (2001) such that the methionine M of YMDD is amino acid 204 of the HBV polymerase. A specific mutation in a protein sequence is represented as "XaaNXbb" where Xaa is the amino acid before the mutation, N is the residue number and Xbb is the mutant amino acid. An "rt" before "XaaNXbb" means "reverse transcriptase". An "s" means "envelope protein".

In accordance with the subject invention it has been found that the mutations rtL80I, rtL82M, rtF166L and rtQ215S are highly correlated with the failure of long-term response to LMV.

In addition, the mutations rtL80I, and rtQ215S are correlated to failure of long-term response to ADV.

Further, the nucleotides changes A1752G/T, T1753C, T1754C, A1762T, G1764A, C1856T, T1858C, C1862T, G1896A, G1898A and G1899A represent point mutations in the precore/core region that correlate with LMV treatment failure. The numbering starts from the unique EcoRI site in HBV (Galibert et al., 1979).

Mutations in the envelope protein at sQ101, sL104, sC107, sS/T114, sT115, sT116, sC121, sK/R122, sT123, sC124, sI/T126, sQ129, sG130, sN/T131, sF/Y134, sP135, sS136, sC137, sC138, sC139, sT/S140, sK141, sP142, sN146, sC147, sT148, sP153, sS154, sS155, sA157, sF/L158, sA/G159, sW163, sS167, and sA/D168 individually or in combination modify the antigenicity of HBsAg leading to escape from vaccine-induced immunity or failure of immunoglobulin therapy or failure of detection in immunoassay.

The subject invention also provides oligonucleotides probes that bind to and detect the HBV nucleic acid markers. As noted above, in one embodiment, the viral marker used to predict the long-term response of a HBV carrier to treatment with nucleotide/nucleoside analogues, or in combination of other anti-HBV agents, is the presence of specific amino acids at specified positions of the HBV polymerase. In one embodiment, the viral markers that predict the long-term response of a HBV carrier to therapy with nucleotide/nucleoside analogues and their combination are: rtL80I, rtL82M, rtF166L and rtQ215S individually or in combination with other mutations such as rtM204I/V/S+/−rtL180M.

The invention also provides a method to assay for the viral markers that predict failure of anti-HBsAg, vaccine escape and immunoglobulin therapy escape. In one embodiment the method comprises isolating nucleic acid from a biological sample and screening for mutation(s) in the sequence encoding the S gene, wherein the presence of mutation(s) selected from, in one embodiment, sQ101, sL104, sC107, sS/T114, sT115, sT116, sC121, sK/R122, sT123, sC124, sI/T126, sQ129, sG130, sN/T131, sF/Y134, sP135, sS136, sC137, sC138, sC139, sT/S140, sK141, sP142, sN146, sC147, sT148, sP153, sS154, sS155, sA157, sF/L158, sA/G159, sW163, sS167, and sA/D168.

Mutations Implicated in the Severity of Liver Disease

Other important diagnostic markers provided according to the subject invention are the mutations in the HBV core promoter and precore/core region at A1752G/T, T1753C, T1754C, A1762T, G1764A, C1856T, T1858C, C1862T, G1896A, G1898A and G1899A. These mutations are implicated in the severity of liver disease progression.

Sato et al. (1995) report the association of core promoter mutations and/or precore mutation in fulminant hepatitis or severe acute hepatitis. The combinations of precore/core mutations we observed in HBVs of LMV-treated patients are:

A1752G, G1896A, rtL180M, rtM204I

T1753C, A1762T, G1764A, C1856T, T1858C, G1898A, G1899A

T1753C, A1762T, G1764A, G1896A, G1899A, rtL180M, rtM204V

T1753C, T1754C, A1762T, G1764A, C1856T, T1858C

T1753C, A1762T, G1764A, T1858C, rtM204I

A1762T, G1764A, T1858C, rtL180M, rtM204V

C1856T, T1858C, G1898A, rtL180M, rtM204V

C1862T, G1896A, G1899A, rtM204I

A1752G, T1858C, rtL180M, rtM204V.

The mutations in the core promoter and precore region are implicated in enhancing viral replication, decreasing HBeAg expression and mutating HBxAg.

Detection of HBV Genotype

The invention further comprises a method to determine the genotype of the HBV in a biological sample.

The genotype A can be defined by the nucleotides: T451 and T586.

The genotype B can be defined by the nucleotides: A321, T324 and G408.

The genotype C can be defined by the nucleotides: A491 and G633.

The genotype D can be defined by the nucleotides: T289, A290 and T867.

The genotype E can be defined by the nucleotides: C705, C706, T837, C840 and C843.

The genotype F can be defined by the nucleotides: A628, T837 and A838.

The genotype G can be defined by the nucleotides: T306, T936 and G939

The genotype H can be defined by the nucleotides: T493, A494, A838, A840, G841 and C842.

For each genotype, two oligonucleotides that span all the bases described would be required and sufficient for proper identification. Genotyping of HBV is important because, for example, HBV genotype affects the course and severity of the liver disease.

In one embodiment, an allele-specific arrayed primer extension (AS-APEX) method (Chan et al, 2004) is used. In another embodiment, each of the oligonucleotide primers is modified to contain phosphorothioate at the 5'-terminus and the allele-specific nucleotide at the 3'-terminus. Oligonucleotide primers are arrayed onto a treated glass slide; strand synthesis or extension will only occur when there is a perfectly matched oligonucleotide and template. No stringent washing is needed to remove unstable complexes as in RDB-ASO hybridization and we have shown that there is no limitation (apart from the size of the glass slide) on the number of mutations that can be simultaneously analysed.

The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

Example 1—Direct Sequencing of Viral Nucleic Acids

Generally, HBV nucleic acids from a biological sample need to be extracted and purified, then amplified, sequenced and then the generated sequence examined for the presence of the markers.

HBV DNA extraction can be accomplished by, for example, proteinase K digestion followed by phenol, phenol/chloroform extraction and ethanol precipitation. Alternatively, any commercial kit utilizing, for example, the silica-gel-membrane technology can be used.

Amplification can be performed by, for example, polymerase chain reaction (PCR; Saiki et al., 1988).

Sequencing can be achieved by the dideoxynucleotide chain termination method also known as the Sanger reaction or by a modified version of the Sanger reaction, the cycle sequencing reaction with fluorescent dideoxynucleotides. Although direct sequencing can detect all mutations, new and known ones, its sensitivity is a drawback. A minor population of resistant mutants needs to reach 20% of the total amount of HBV quasispecies pool before it can be detected.

Example 2—Detection Via Oligonucleotide Probes

Detection of variants or mutants by oligonucleotides methods is much more sensitive than direct sequencing. Minor populations of variants as low as 5% of the total HBV population can be identified, as in the early emergence of mutants, before manifestation of clinical resistance.

By using a panel of oligonucleotides to simultaneously detect a number of mutations or sequence variations, with the enhanced sensitivity, the method allows prediction of resistance to other classes of nucleoside/nucleotide analogues.

1. Reverse Dot Blot Hybridization

Oligonucleotide probes, designed to detect the viral markers for long-term response to anti-HBV therapy, for immune escape, and for genotyping, can be arrayed on membranes or preferably glass slides then hybridized to amplified and labeled HBV nucleic acids. Following hybridization, the membrane or slide is washed at high stringency. The result of the hybridization reaction is then visualized.

Preferably, the diagnostic nucleotide(s) in this instance are located at the central section of the oligonucleotide.

Labeled HBV targets complementary to the oligonucleotides can be produced in an asymmetric PCR reaction or strand specific degradation.

The label attached to the complementary HBV nucleic acid can be biotin where visualization entails formation of complex with strepavidin-horseradish peroxidase/alkaline phosphatase and color development with substrate such as 4-chloro-3-naphtol or BICP-NBT. Alternatively, a fluorescent label can be used and the signal is acquired by using a laser scanner. Radioactive or chemiluminescent labels can also be used with their respective method of signal detection.

2. Allele Specific Arrayed Primer Extension

A comprehensive HBV array is employed for the simultaneous analysis of all or most of the known HBV variants of interest. In one embodiment, the HBV variants include 8 HBV genotypes, 5 precore, 2 core-promoter mutations, 23 S gene and 45 polymerase gene mutations. This method allows the detection of viral mutants and genotypes in the patients' serum samples.

In this method, the diagnostic nucleotide(s) can be located at the 3' end of the oligonucleotide. The complementary single strand HBV targets are produced by an asymmetric PCR reaction.

The panel of oligonucleotides is arrayed onto glass slides then is subjected to hybridization with the HBV targets in a reaction that includes: buffer, a thermostable polymerase and dNTPs one of which is labeled, preferably in the form of biotin-dUTP or a fluorescent tagged dUTP. During the hybridization reaction, primer extension occurs when the oligonucleotides are perfectly matched at the 3' end to their HBV targets. The slide is washed after the hybridization/extension reaction to remove the un-incorporated dNTPs. The signal is then acquired by detecting the labeled nucleotide incorporated in the newly synthesized strand.

For each nucleotide position to be interrogated, at least two oligonucleotide primers are needed, one oligonucleotide primer for the normal sequence and one oligonucleotide primer for the mutant sequence. Multiple nucleotide mutations at one nucleotide position would require the same number of mutant oligonucleotides. The primers are tethered at the 5' end by covalent linkage to the solid surface, in this instance, the glass slide and the 3' end is free to hybridize and terminates at the base complementary to the diagnostic base in the HBV target sequence or up to two bases beyond the diagnostic base.

The HBV targets complementary to the oligonucleotides are prepared by asymmetric amplification or by strand specific degradation, followed by purification and concentration.

The hybridization/extension reaction combines the discriminative effect of hybridization with the base-pairing specificity of polymerase. A solution containing the HBV target DNA, buffer, dATP, dGTP, dCTP, biotin-dUTP or fluorescently tagged dUTP and a thermostable polymerase is overlaid on top of the arrayed oligonucleotide primers. Extension occurs only if the 3' bases of the oligonucleotide primer are in perfect match with the target; the labeled dUTP is incorporated in the extended strand. Oligonucleotides/targets mismatches will give negative results.

The reaction is stopped by washing and signal acquisition is performed according to the label used in the extension reaction.

In one embodiment, samples from 100 unrelated patients whose HBV mutations have been determined by existing commercial kits were obtained. 46 samples gave concordant result with both the existing techniques and the technique of the present invention. 11 samples had discordant results and DNA fragments of these samples containing the rt-polymerase HBV gene were cloned into plasmids, and sequenced to confirm the results of the array analysis. 43 samples were found to yield additional mutations by the array analysis in the present invention. The presence of these additional mutations was confirmed also by sequencing. This shows the array in the present invention is more sensitive in detecting emerging mutants.

In one embodiment, serum samples from 22 HBV patients on antiviral therapy were collected before initiation of therapy and during a 2 to 5-years follow-up period and assayed using the HBV array. Results indicated that the array can detect mutations in samples with <70 copies/ml HBV DNA. It was able to detect mutations that confer drug resistance 3 to 7 months prior to existing commercial kits. Therefore, the present invention enables doctors to detect drug resistance at an earlier time, and, if appropriate, employ an alternative drug before overt biochemical relapse occurs.

In one patient, the presence of LMV resistant mutation 78T was noted in his 'naïve' serum sample (taken before initiation of antiviral therapy). Other LMV resistant HBV mutant strains 180M, 200V and 204V were detected 14 months after treatment. With this array, it is therefore possible to predict a patient's eventual resistance to certain anti-viral agent so that an alternative drug may be used at the onset of therapy.

3. Array Method for Naked Eye Visualization of Array Results

This method is applicable to both the reverse dot blot and the allele-specific primer extension formats. The label of choice is biotin. In the reverse dot blot procedure, biotin-dUTP or biotin labeled primers are used to amplify the HBV targets. In the extension method, biotin-dUTP is used in the in-situ strand extension on the glass array.

In this embodiment, a robotic printer is used; each oligonucleotide is printed six times in a tight cluster (3×2) to generate a localized deposit of oligonucleotide or spot, to create spots large enough and spaced far enough from each other that allows the detection of the individual spots without the aid of microscope or elaborate magnifying equipment.

Spots arrangement may be in the form of a grid composed of rows and columns, preferably with the mutant oligonucleotide printed below the normal oligonucleotide.

The invention also provides an ordered arrays of oligonucleotides in which different oligonucleotides occupy different locations such that each is addressable by its coordinates or location on the array.

Following the hybridization or hybridization/extension reaction, the array is washed to remove the unbound targets or un-incorporated nucleotides. A solution of strepavidin conjugated alkaline phosphatase is overlaid on the array. The alkaline phosphatase is complexed to the biotin in the hybridized targets or the newly synthesized strands through the strepavidin. Excess alkaline phosphatase is washed away; the array is then incubated with a substrate such as BCIP-NBT that yields a blue-violet precipitate upon catalysis by alkaline phosphatase. The color precipitation is stopped by washing, and the array is dried. For documenting the result, the array can be photographed with a digital camera or scanned with a flatbed desktop scanner.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

REFERENCES

Allen M I, Deslauriers M, Andrews C W, Tipples G A, Walters K A, Tyrrell D L, Brown N, Condreay L D., Identification and characterization of mutations in hepatitis B virus resistant to lamivudine. Lamivudine Clinical Investigation Group. Hepatology. 1998 June; 27 (6):1670-7.

Chan K, Wong M S, Chan T K, Chan V., A thalassaemia array for Southeast Asia. Br J Haematol. 2004 January; 124 (2):232-9.

Galibert F, Mandart E, Fitoussi F, Tiollais P, Charnay P., Nucleotide sequence of the hepatitis B virus genome (subtype ayw) cloned in E. coli., Nature. 1979 October; 281 (5733):646-50.

Kazim S N, Chauhan R, Das B C, Sarin S K., Association of core promoter mutations with viral breakthrough in chronic hepatitis B patients on long-term lamivudine therapy. J Gastroenterol Hepatol. 2006 October; 21 (10): 1525-32.

Liaw Y F, Sung J J Y, Chow W C, Farrell G, Lee C-Z, Yuen H, Tanwandee T, Tao Q-M, Shue K, Keene O N, Dixon J S, Gray F, Sabbat J, for the Cirrhosis Asian Lamivudine Multicentre Study Group., Lamivudine for patients with chronic hepatitis B and advanced liver disease. N Engl J of Med., 2004 October; 351 (15):1521-31.

Perz J F, Armstrong G L, Farrington L A, Hutin Y J, Bell B P., The contributions of hepatitis B virus and hepatitis C virus infections to cirrhosis and primary liver cancer worldwide. J Hepatol. 2006 October; 45 (4): 529-38.

Saiki R K, Gelfand D H, Stoffel S, Scharf S J, Higuchi R, Horn G T, Mullis K B, Erlich H A., Primer-directed enzymatic amplification of DNA with a thermostable DNA polymerase. Science. 1988 January; 239 (4839): 487-91.

Sato S, Suzuki K, Akahane Y, Akamatsu K, Akiyama K, Yunomura K, Tsuda F, Tanaka T, Okamoto H, Miyakawa Y, Mayumi M., Hepatitis B virus strains with mutations in the core promoter in patients with fulminant hepatitis. Ann Intern Med. 1995 February; 122 (4):241-8.

Stuyver L J, Locarnini S A, Lok A, Richman D D, Carman W F, Dienstag J L, Schinazi R F., Nomenclature for antiviral-resistant human hepatitis B virus mutations in the polymerase region. Hepatology. 2001 March; 33 (3): 751-7.

Torresi J, Earnest-Silveira L, Deliyannis G, Edgtton K, Zhuang H, Locarnini S A, Fyfe J, Sozzi T, Jackson D C., Reduced antigenicity of the hepatitis B virus HBsAg protein arising as a consequence of sequence changes in the overlapping polymerase gene that are selected by lamivudine therapy. Virology. 2002 February; 293 (2): 305-13.

Weber B., Genetic variability of the S gene of hepatitis B virus: clinical and diagnostic impact. J Clin Virol. 2005 February; 32 (2): 102-12.

We claim:

1. A kit for detecting, simultaneously, mutations and genotypes of hepatitis B virus (HBV) variants to determine whether an HBV isolate exhibits reduced sensitivity to one or more anti-HBV compounds and/or to determine whether the genotype of an HBV isolate influences the course and severity of liver disease, the kit comprising an HBV array that comprises a plurality of oligonucleotide primers, which oligonucleotide primers are tethered at a 5' end by covalent linkage to a solid surface and free at a 3' end to hybridize; wherein the 5' end of each of the plurality of oligonucleotide primers comprises nucleotides that form a hairpin structure and contain a phosphorothioate moiety; and which oligonucleotide primers terminate at their 3' end at a nucleotide complementary to a diagnostic nucleotide or up to two nucleotides beyond a diagnostic nucleotide, wherein the 3' end of at least one oligonucleotide primer comprises at least one nucleotide that anneals to a diagnostic nucleotide comprising a HBV genotype of interest, and wherein the array enables simultaneous detection of the plurality of HBV genotypes and HBV mutations of interest.

2. The kit according to claim 1, wherein said plurality of oligonucleotide primers comprise a first oligonucleotide primer and a second oligonucleotide primer,
wherein the 3' end of the first oligonucleotide primer comprises nucleotides that anneal to a target HBV nucleic acid sequence comprising a mutation of interest, and
wherein the 3' end of the second oligonucleotide primer comprises nucleotides that anneal to a corresponding HBV nucleic acid sequence that does not contain the mutation of interest.

3. The kit according to claim 1, further comprising deoxynucleotides.

4. The kit according to claim 3, wherein the deoxynucleotides comprise dATP, dGTP, dCTP, and dUTP.

5. The kit according to claim 4, wherein at least one of the dATP, dGTP, dCTP, and dUTP is labeled.

6. The kit according to claim 5, wherein at least one of the dATP, dGTP, dCTP, and dUTP is biotin-labeled or fluorescently labeled.

7. The kit according to claim 5, wherein the dUTP or dCTP is labeled.

8. The kit according to claim 1, further comprising thermostable polymerase molecules.

9. The kit according to claim 1, further comprising buffer and/or cover slips.

10. The kit according to claim 1, further comprising one or more agents for colorimetric reaction.

11. The kit according to claim 10, wherein the agent for colorimetric reaction is selected from streptavidin alkaline phosphatase, horseradish peroxidase, BCIP/NBT, or 4-Chloro-1-naphthol.

12. The kit according to claim 1, wherein the plurality of oligonucleotides are linked to a solid surface via the phosphorothioate moiety.

13. The kit according to claim 12, wherein the solid surface is a glass slide.

* * * * *